US00PP08485P

United States Patent [19]

Bubani

[11] Patent Number: Plant 8,485

[45] Date of Patent: Dec. 7, 1993

[54] "SANTA MARIA" NECTARINE TREE

[75] Inventor: Giovanni B. Bubani, 921 N. Peach Ave., Apt. #119, Fresno, Calif. 93727-2492

[73] Assignee: Giovanni B. Bubani, Fresno, Calif.

[21] Appl. No.: 941,531

[22] Filed: Sep. 8, 1992

[51] Int. Cl.[5] ..... A01H 5/00
[52] U.S. Cl. ..... Plt./41.3
[58] Field of Search ..... Plt./41.3

*Primary Examiner*—James R. Feyrer

*Attorney, Agent, or Firm*—Worrel & Worrel

[57] ABSTRACT

A new and distinct variety of nectarine tree which is somewhat remotely similar to the "Fantasia" nectarine tree (unpatented) in producing freestone fruit, but from which it is distinguished in that the fruit are mature for harvesting and shipment approximately two weeks after the fruit produced by the "Fantasia" nectarine tree and wherein the fruit has a brighter red blush coloration, firmer flesh and enhanced flavor and quality than the fruit of the "Fantasia" nectarine tree.

1 Drawing Sheet

BACKGROUND OF THE NEW VARIETY

The present invention relates to a new and distinct variety of nectarine tree, which will hereinafter be denominated varietally as "Santa Maria", and, more particularly, to a nectarine tree which produces freestone fruit which are mature for commercial harvesting and shipment approximately July 21 to August 3 in the San Joaquin Valley of central California, and which is further distinguished in that the fruit are of large size with a bright red blush coloration and excellent flavor and flesh characteristics.

ORIGIN AND ASEXUAL REPRODUCTION OF THE NEW VARIETY

The present variety of nectarine tree was discovered by the applicant in his orchard which is located near Sanger in the central San Joaquin Valley of California. The applicant discovered the new variety in 1983 as an open pollinated seedling of the unpatented "Larry's" nectarine tree (unpatented). The seedling of the instant invention was discovered on the applicant's Ranch No. 11 on Goodfellow Avenue near Sanger, Calif.

In the month of September, 1983, the applicant asexually reproduced the seedling of the new variety by grafting four trees to the new variety using buds from the parent seedling of the new variety. The asexually reproduced trees of the new variety were grown on the Gong Ranch of the applicant near Sanger, Calif. Over the years thereafter, the applicant closely observed the asexually reproduced trees of the instant invention and confirmed that they were in all respects identical to the parent tree of the new variety.

SUMMARY OF THE NEW VARIETY

The "Santa Maria" nectarine tree is characterized as to novelty by producing freestone fruit late in the season which are large in size exhibiting a bright red blush coloration and with excellent flavor and flesh characteristics. The fruit produced by the "Santa Maria" nectarine tree are ripe for commercial harvesting and shipment approximately July 21 to August 3 in the San Joaquin Valley of central California. The new variety is most closely similar to the "Fantasia" nectarine tree (unpatented) which is believed to be the latest high volume freestone nectarine tree grown in California. All high volume nectarines maturing after the "Fantasia" nectarine tree are of the clingstone type. The date of maturity for the "Fantasia" nectarine tree in 1990 grown in Sanger-Reedley fruit district of central California was July 6 to July 19. For the new variety, the date of maturity was July 21 to August 3 in the same fruit growing district, or approximately two weeks after the "Fantasia" nectarine tree.

In addition to the later date of maturity, the fruit of the new variety excels in comparison with the fruit of the "Fantasia" nectarine tree in several respects. The fruit of the new variety has a brighter red blush coloration in comparison with the more dull orange-red blush coloration of the "Fantasia" nectarine tree. Also, the percentage of blush present on the fruit of the new variety is greater than that found on the fruit of the "Fantasia" nectarine tree. With respect to the firmness of the fruit, the new variety possesses a firmer flesh quality than the fruit of the "Fantasia" nectarine tree and is less prone to tip softening or tip "slipskin" which can be a substantial problem with the fruit of the "Fantasia" nectarine tree.

Furthermore, with regard to production, in many years the "Fantasia" nectarine tree displays a substantial preharvest fruit drop. This drop can occur after thinning has been completed up to two weeks before harvest and usually results in reduced yields. No such drop has been observed with the new variety, giving it the advantage of a greater yield potential over the "Fantasia" nectarine tree.

Lastly, the flavor and quality of the fruit of the new variety is outstanding. Its high solids and intense flavor are a substantial improvement over the very average flavor characteristics of the fruit of the "Fantasia" nectarine tree.

BRIEF DESCRIPTION OF THE DRAWING

The drawing is a color photograph of mature fruit of the new variety including a first specimen so positioned as to show the base end portion thereof; a second shown in side elevation; a third so positioned as to show the apex end portion thereof; and a fourth sectioned and laid open to show the stone in position in one of the sections and to expose the pit well of the other of the sections; and representative foliage of the new variety.

DETAILED DESCRIPTION

Referring more specifically to the pomological details of this new and distinct variety of nectarine tree, the following has been observed under the ecological conditions prevailing at the orchard of origin which is located near Sanger, Calif. All major color code designations are by reference to the *Dictionary of Color*, by Maerz and Paul, published in 1950. Common color names are also occasionally employed.

TREE

Generally: Hardy.
- *Figure.*—Upright to upright-spreading with eventual form and density determined by pruning.
- *Productivity.*—Productive.
- *Regularity of bearing.*—Regular.

Trunk:
- *Size.*—Average in diameter.
- *Surface texture.*—Average in comparison with other common nectarine varieties.
- *Color.*—Grey-brown (7-C-9).
- *Lenticels — numbers.*—Numerous present on trunk surface.
- *Lenticels — size.*—Large. The lenticel openings are surrounded by light hazel-brown (13-J-9) callous tissue.

Branches:
- *Size.*—Average.
- *Surface texture.*—Average.
- *Color — one year of age or older wood.*—Light brown (7-C-10).
- *Color — immature branches.*—Light green (21-L-5) with shoots exposed to direct sunlight displaying reddish pigmentation.
- *Surface texture — immature growth.*—Smooth.

LEAVES

Size:
- *Generally.*—Large. Leaf measurements have been taken from leaves growing near midpoint of vigorous upright current season's growth.
- *Average length.*—18.4 cm (4.674 inch), including the petiole.
- *Average width.*—4.5 cm (1.143 inch).

Form: Lanceolate with acuminate leaf apex. The apex is often slightly twisted to one side.

Color:
- *Upwardly disposed surface.*—Deep green (24-E-8).
- *Downwardly disposed surface.*—Lighter grey-green (23-J-3).
- *Leaf vein.*—Color of midvein on lower leaf surface is a light green-yellow (20-G-2).

Marginal form:
- *Generally.*—Crenate, often doubly so at mid-leaf. Individual crenations are low and moderately broad.

Leaf margin: Moderately undulate.

Petiole:
- *Size.*—Medium.
- *Length.*—Average 11.5 mm (0.4527 inches).
- *Thickness.*—Average 2.0 mm (0.0787 inches).
- *Color.*—Light green (20-I-2).

Stem glands:
- *Form.*—Most glands present are of reniform type.
- *Position.*—Most commonly, 3 to 5 glands are present with 2 to 4 found on the petiole.
- *Pattern.*—In alternate position and an additional 1 to 2 percent on the base of the leaf margin. Substantial variation exists. Globose glands are occasionally present, but only on the petiole.
- *Color.*—Shiny light green (18-K-3) when young, darkening and deteriorating with age.

Stipules: Two moderately large stipules present, but they are early deciduous.
- *Length.*—8 mm (0.3149 inches) to 10 mm (0.3937 inches).
- *Color.*—Light green (18-K-4) when young, darkening substantially with age.
- *Form.*—Serrate.

FLOWERS

Bloom quantity: Abundant. Most commonly 2 flower buds are present per node.

Flower buds:
- *Size.*—Medium.
- *Form.*—Conic.

Bud scales: Covered with a moderately long, grey pubescence.
- *Color.*—Light chestnut brown (Rustic Brown 7-H-11).

Flowers:
- *Generally.*—Large and showy in form.

Size:
- *Diameter.*—Average 39 mm (1.535 inches) when fully expanded.

Date of full bloom: March 1 in 1991. The bloom timing is considered average to slightly early in relation to other common commercial nectarine cultivars.

Petal:
- *Number.*—Five.
- *Color.*—Pink (1-D-1) with darker shades of pink (1-F-1) basally and very dark pink (1-G-2) on the claw.
- *Form.*—Generally ovate.
- *Length.*—Averages 19.5 mm (0.7677 inches).
- *Width.*—Averages 16.2 mm (0.6377 inches).
- *Petal claw.*—Relatively short, broad and truncate. The petals are slightly cupped inwards.
- *Margins.*—Slightly undulate.
- *Apex.*—Rounded with no tip.

Pedicel:
- *Generally.*—Glabrous.
- *Color.*—Shiny medium green (18-L-5).
- *Length.*—Short, averaging 2.0 mm (0.0787 inches).
- *Thickness.*—Averages 2.0 mm (0.0787 inches).

Nectaries:
- *Color.*—Bright orange (9-J-10).

Anthers:
- *Size.*—Average.
- *Color.*—Tan (9-G-3) ventrally and red streaked (Withered Rose 5-J-10) dorsally.

Pollen: Abundant.
- *Color.*—Yellow (10-L-3).

Stamens:
- *Filament color.*—Very light pink (1-B-1) when young, darkening to a light violet color (2-F-3) when fully mature.
- *Length.*—13 mm (0.5118 inches) to 14.5 mm (0.5708 inches), about equal with the pistil at full maturity.

Pistil: Glabrous.
- *Color.*—Very light green (18-J-2).
- *Length.*—16.5 mm (0.6496 inches) including the ovary when fully extended.

FRUIT

Maturity when described: Ripe for commercial harvesting and shipment approximately July 21 to August 3 near Sanger, Calif. in 1990.

Size:

*Generally.*—Uniform, large in size.

*Average diameter in the axial plane.*—78 mm (3.070 inches) to 82 mm (3.228 inches).

*Average diameter in the suture plane.*—72 mm (2.834 inches) to 78 mm (3.070 inches).

*Average cheek diameter.*—72 mm (2.834 inches) to 75 mm (2.952 inches).

Form:

*Uniformity.*—Uniform.

*Lateral.*—Slightly ovate to an irregular oval.

*Axial.*—Globose to oval.

Suture:

*Generally.*—A broad, rather shallow but distinct depression from apex to base, more distinct apically. The suture usually takes on the general color of the adjacent skin area, but the general color is overlain with some very thin multiple striping in various shades of red, most commonly a dark Korean red (5-J-11). The thin striping is only present along the ventral suture area. A distinct depression is evident on the dorsal side of the apex and over the dorsal apical shoulder.

Ventral surface:

*Generally.*—Rounded and moderately lipped, especially apically. One side of the fruit usually protrudes more than the other, especially in the upper apical shoulder area.

Stem cavity:

*Generally.*—Moderately small in size.

*Width.*—Averages 24 mm (0.9448 inches) to 27 mm (1.062 inches).

*Depth.*—Averages 12 mm (0.4724 inches) to 14 mm (0.5511 inches).

*Length.*—25 mm (0.9842 inches) to 29 mm (1.141 inches).

*Shape.*—Oval to almost globose. The basal shoulders of many fruit show an indentation mark where the fruit was pressed against the bearing branch.

Base:

*Form.*—Slightly truncate. Base angle can be somewhat variable, but most frequently is slightly oblique to the fruit axis.

Apex:

*Shape.*—Apex form is generally rounded, but apex height can be variable. At times a low tip is present, higher than the apical shoulders. The tip can also, however, be in a depressed form, lower than the apical shoulders and recessed into the suture groove.

Pistil point:

*Form.*—Variable in form, from perfectly apical to quite oblique.

Stem:

*Length.*—Medium to slightly short from 10 mm (0.3937 inches) to 12 mm (0.4724 inches).

*Thickness.*—Average, from 3.5 mm (0.1377 inches) to 4.0 mm (0.1574 inches).

*Color.*—Light green (20-K-6).

Skin:

*Thickness.*—Average.

*Texture.*—Tenacious to flesh at commercial maturity. Glabrous with a bright, glossy finish.

*Tendency to crack.*—None observed.

*Blush color.*—Variable, covering from 25 to 60 percent of the fruit surface. Blush pattern is generally a solid washed form, overlain with some color streaking and dappling. Blush color occurs within a range from a medium Canna antique red (4-J-11) to a darker Egyptian red (6-L-11), including a range of intensities in between. Most blushed areas are overlain with a dark red (5-K-11) dappling and/or striping.

*Ground color.*—Light yellow (10-K-3) to yellow-green (18-J-1).

*Flesh color.*—Interior coloration of the flesh is a clear light yellow (10-J-2).

*Stone cavity — color.*—Dark red (6-J-11) on the walls of the cavity and radiating inward into the flesh 5 mm (0.1960 inches) to 8 mm (0.3149 inches). A moderate amount of white callous tissue is present on the walls of the stone cavity.

*Flavor.*—Outstanding, mild.

*Aroma.*—Slight.

*Texture.*—At commercial maturity, the flesh is firm and crisp.

*Fibers — numbers.*—Moderate of medium length, light colored fibers are present.

*Ripening.*—Ripens evenly.

*Eating quality.*—Excellent.

Stone:

*Attachment.*—Full freestone.

*Fibers — numbers.*—Few and relatively short. Most are attached basally.

*Size.*—Medium.

*Size — length.*—38.2 mm (1.503 inches).

*Size — width.*—24.6 mm (0.9685 inches).

*Size — thickness.*—17.8 mm (0.7007 inches).

*Form — generally.*—Variable, from a long oval to slightly obovate.

*Apex — shape.*—Acute in form with usually a sharp acuminate tip.

*Color — dry.*—Medium brown (7-E-11). Moderate amount of callous tissue is present, usually attached within the stone pits, especially laterally.

*Base — shape.*—Broad and truncate in form. Base angle variable but most often very slightly oblique to the stone axis.

*Sides — generally.*—Variable, from equal to slightly unequal in size.

*Surface.*—Moderately rough with deep grooves over the apical shoulders laterally, and substantially grooved basally and also along the basal portion of the dorsal suture. Deep pits are present laterally at mid-stone.

*Ventral edge.*—Rather broad, especially at mid-suture. Several low, thick wings are present along the ventral suture, converging apically.

*Dorsal edge.*—A wide groove is usually present extending from the base to 9 mm (0.3543 inches) to 13 mm (0.511 inches) above the base. The groove becomes narrow at mid dorsal suture, and the ridges subtending the groove become raised and are irregularly cut with cross grooves at mid-stone. The apical shoulder of the dorsal edge is moderately eroded with the shoulder taking on a concave appearance.

*Hilum.*—Large and substantially eroded. Generally oval in form.

*Tendency to split.*—None observed.

Use: A late season fresh market nectarine for both local market and long distance shipping.

Although the new variety of nectarine tree possesses the described characteristics noted above as a result of the growing conditions prevailing near Sanger, Calif. in the central part of the San Joaquin Valley of California, it is to be understood that variations of the usual magnitude and characteristics incident to changes in growing conditions, irrigation, fertilization, pruning and pest control are to be expected.

Having thus described and illustrated by new variety of nectarine tree, what I claim as new and desire to be secured by Plant Letters Patent is:

1. A new and distinct variety of nectarine tree substantially as illustrated and described and which is somewhat remotely similar to the "Fantasia" nectarine tree (unpatented), but from which it is distinguished by producing freestone fruit which are mature for commercial harvesting and shipment after the fruit of the "Fantasia" nectarine tree, or approximately July 21 to August 3 in the San Joaquin Valley of central California, and which are larger in size, more highly colored and with enhanced flavor and flesh characteristics when compared with the fruit of the "Fantasia" nectarine tree.

* * * * *

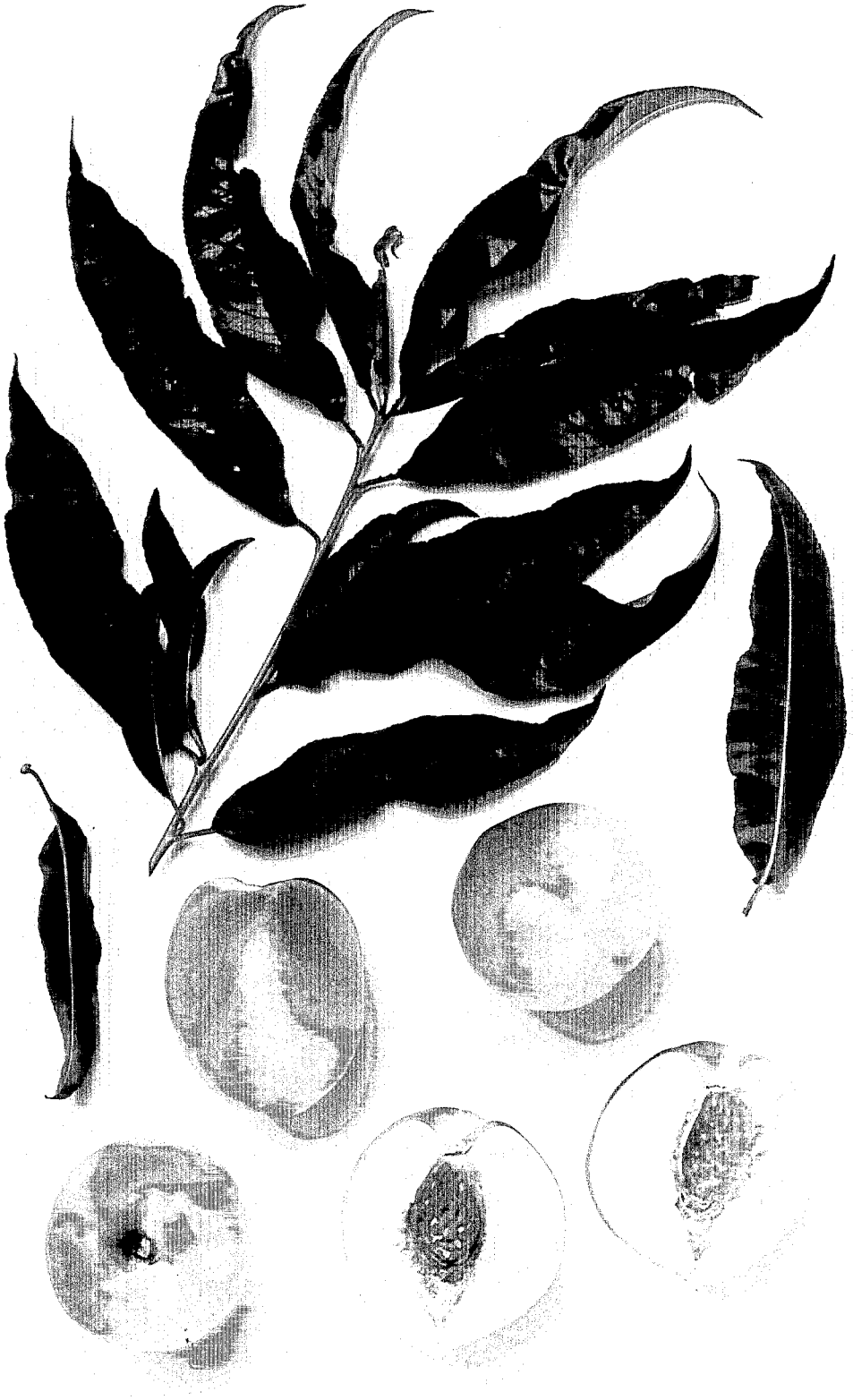

UNITED STATES PATENT AND TRADEMARK OFFICE

CERTIFICATE OF CORRECTION

PATENT NO. : Plant 8,485

DATED : December 7, 1993

INVENTOR(S) : Giovanni Bosco Bubani

It is certified that error appears in the above-indentified patent and that said Letters Patent is hereby corrected as shown below:

On the Title Page:

Item [19], delete "Bubani" and insert --Bosco Bubani--.
Item [75], delete "B." and substitute --Bosco--.
Item [73], delete "B." and substitute --Bosco--.

Signed and Sealed this

Twenty-first Day of June, 1994

*Attest:*

Bruce Lehman

BRUCE LEHMAN

*Attesting Officer*

*Commissioner of Patents and Trademarks*